United States Patent

Scannell et al.

[11] 3,956,067
[45] May 11, 1976

[54] ANTIBIOTIC X-372A

[75] Inventors: James P. Scannell; David L. Pruess, both of North Caldwell; Thomas C. Demny, Livingston, all of N.J.

[73] Assignee: Hoffmann-La Roche Inc., Nutley, N.J.

[22] Filed: May 28, 1975

[21] Appl. No.: 581,453

Related U.S. Application Data

[62] Division of Ser. No. 504,936, Sept. 11, 1974, Pat. No. 3,901,880.

[52] U.S. Cl............................................. 195/80 R
[51] Int. Cl.²......................................... C12D 9/00
[58] Field of Search .................................. 195/80 R

[56] References Cited
UNITED STATES PATENTS

| | | | |
|---|---|---|---|
| 3,743,580 | 7/1973 | Umezawa et al.................. | 195/80 R |
| 3,775,255 | 11/1973 | Berger et al. ..................... | 195/80 R |

*Primary Examiner*—A. Louis Monacell
*Assistant Examiner*—Robert J. Warden
*Attorney, Agent, or Firm*—Samuel L. Welt; George M. Gould; Frank P. Hoffman

[57] ABSTRACT

The invention relates to a new and useful antibacterial substance which is of the formula

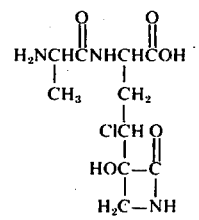

and to processes for its production and recovery. The invention embraces this antibacterial agent and its crude concentrates, as purified solids and in pure crystalline forms. The antibiotic of Formula I is effective in inhibiting the growth of gram-negative and gram-positive bacteria. The compound of Formula I is prepared by cultivating a strain of Streptomyces species 372A in an aqueous carbohydrate solution containing a nitrogenous nutrient under submerged aerobic conditions until substantial activity versus gram-positive and gram-negative bacteria is imparted to said solution and then recovering said compound of Formula I from the solution.

1 Claim, No Drawings

ANTIBIOTIC X-372A

This is a division of application Ser. No. 504,936 filed Sept. 11, 1974, now U.S. Pat. No. 3,901,880.

DETAILED DESCRIPTION OF THE INVENTION

There is provided according to the present invention, an antibiotic substance effective in inhibiting the growth of gram-positive and gram-negative bacteria which is of the Formula I. Chemically this substance is known as (s)-Alanyl-3-[α-(s)-Chloro-3-(s)-Hydroxy-2-oxo-Azetidinylmethyl]-(s)-Alanine.

There is further provided according to the present invention, a process for the production of such antibiotic substance of the Formula I which comprises cultivating a strain of Streptomyces sp. 372A in an aqueous carbohydrate solution containing a nitrogenous nutrient under submerged aerobic conditions until substantial activity versus gram-negative and gram-positive bacteria is imparted to said solution and then recovering said compound of the Formula I from said solution.

The organism producing the antibiotic of the present invention was isolated from a sample of soil collected from an outdoor planter in Piscataway, N.J., and is a new species designated Streptomyces species 372A. A culture of the living organism, given the laboratory designation 372A, has been deposited in the Northern Regional Research Labs, Peoria, Ill. and added to its permanent collection of microorganisms as NRRL 8045.

The representative strain of Streptomyces ap. 372A has been characterized as follows:

The formulation of the media used in the description of the growth characteristics, is described below.

Medium 1: "Fermentation medium": Difco Bacto Thermoactinomyces fermentation medium to which 1.5% agar was added.

Medium 2: BBL(Baltimore Biological Laboratory) Czapek-Dox broth, to which 1.5% agar was added.

Medium 3: Difco Bacto potato dextrose agar.

Medium 4: "Y+M medium": yeast extract, 0.4%; malt extract, 1.0% dextrose, 0.4%; agar, 2%; pH 7.3.

Medium 5: "Oatmeal-glucose medium": Gerber's oatmeal, 5%; dextrose, 2%; agar 2% in tap water; pH 7.0.

Medium 6: "Tomato paste medium": dextrose, 1%; $K_2HPO_4$, 0.1%; tomato paste, 2%; Wilson's Medopeptone, 0.1%; $CaCO_3$, 0.2%; agar, 1.5% in tap water; pH 6.8–7.3.

Medium 7: "Tomato-soy medium": same as medium 6, to which 1% soyalose (Central Soya Co.) has been added.

Medium 8: "Pablum medium": 6% Pablum mixed cereal in cheesecloth bag dipped in and out of boiling tap water for 2 or 3 minutes. The water lost by evaporation is replaced, and agar is added to 1.5%.

Medium 9: "Tomato-oatmeal medium": baby oatmeal (Gerber's), 2%; tomato paste, 2%; agar, 2%, in tap water; pH 6.8–7.3.

Medium 10: "Yeast extract medium": yeast extract, 1%; dextrose, 1%; agar, 1.5%, in tap water; pH 6.8.

Medium 11: "Glucose-asparagine medium": dextrose, 1%; asparagine, 0.05%; $K_2HPO_4$, 0.05%; agar, 1.5%; pH 6.8.

Medium 12: "Glycerol-asparagine medium": glycerol, 1%; asparagine, 0.1%; $K_2HPO_4$, 0.1%; agar, 2% in tap water; pH 7.0.

Medium 13: "Starch-casein medium": soluble starch, 1%; casein, 0.1%; $K_2HPO_4$, 0.05%; $MgSO_4$, 0.05%; agar, 1.5%; pH 7.4.

Medium 14: "Emerson's medium": beef extract, 0.4%; peptone, 0.4%; NaCl, 0.25%; yeast extract, 0.1%; dextrose, 1%; agar, 2%; pH 7.0.

Medium 15: "Bennett's medium": yeast extract, 0.1%; beef extract, 0.1%; N-Z-Amine A (casein hydrolysate from Sheffield Inc.) 0.2%; dextrose, 1%; agar, 1.8%; pH 7.3.

Medium 16: "Amidex medium": Amidex (Corn Products Co., Decatur, Ill.) 1%; N-Z-Amine A, 0.2%; beef extract, 0.1%; yeast extract, 0.1%; $CaCl_2$, $2H_2O$, 0.0014%; agar, 2%; pH 7.3.

Medium 17: "Sporulation medium" (ATCC medium number 5): yeast extract, 0.1%; beef extract, 0.1%; tryptose 0.2%; glucose, 1%; $FeSO_4$, trace; agar, 1.5%; pH 7.2.

Media 18, 19, 20, 21, 22, 23 are, respectively, media 2 through 7 as described by Shirling, E. B., and Gottlieb, D., Methods for characterization of Streptomyces species, International J. of Systematic Bacteriol., 16, 331–340, 1966.

| Medium | Characteristics of aerial growth | Color of upper surface of colonies | Color of reverse of colonies |
|---|---|---|---|
| 1 | abundant, with good sporulation pale brown diffusible pigment | pallid neutral gray with white specks | blackish brown with drab edges; later the edge change to Verona brown |
| 2 | good growth and sporulation | pale quaker drab with secondary sporulation over light brown vegetative mycelium | grayish olive |
| 3 | no growth | | |
| 4 | abundant, with good sporulation; pale brown pigment diffuses into medium | pale neutral gray center to pallid neutral gray toward the edges; later pale olive gray center olive gray toward edges, and pallid neutral gray edges | blackish brown |
| 5 | very poor growth | | |
| 6 | abundant, wrinkled | pallid neutral gray; later, center pale gull gray, and light gull gray toward edges | blackish brown; later the edges become drab color |
| 7 | abundant, wrinkled, somewhat coarse, with good sporulation | center pallid purplish gray and pale purplish gray toward the edges; | blackish brown |

-continued

| Medium | Characteristics of aerial growth | Color of upper surface of colonies | Color of reverse of colonies |
|---|---|---|---|
| | | later pallid neutral gray center, and pallid neutral gray toward edges, with light mouse gray edges | |
| 8 | abundant, smooth and raised with slightly undulated edges; good sporulation | pale mouse gray with many white specks, turning off-white time | olivaceous black |
| 9 | abundant, wrinkled; slight clearing of medium around | light mouse gray center and pallid mouse gray with white spots toward edges; pale mouse gray sectors appear with age | blackish brown |
| 10 | abundant, tightly undulated; good sporulation; brown pigment diffusing into medium | mouse gray with few tiny white specks; thinly sporulated edges are mouse gray | black, with auburn indentations |
| 11 | abundant, fairly smooth, with some granules; good sporulation agar cracks underneath colonies with age | pale olive gray center, with off-white edges, later, pale-mouse gray sporulation areas, and dark olive buff vegetative mycelium | dark olive gray, with cartridge buff edges |
| 12 | abundant, fairly smooth, with granules; pale brown pigment excreted; agar cracks with age | slightly mottled light mouse gray center, becoming pallid mouse gray toward edges; later light olive gray center, off-white toward edges, with chaetura drab vegetative mycelium and pale drab edges | drab center, changing to blackish brown and cartridge buff toward edges |
| 13 | abundant, smooth, with some granules; good sporulation; milky white precipitate around the colonies | mouse gray center, changing to light mouse gray toward edges, with off-white edges; with age, these have segments of hair brown mycelium | grayish olive, turning to grayish olive and pale olive gray toward the edges |
| 14 | abundant, slightly undulated; good sporulation; pale brown pigment diffuses into medium | pale and pallid mouse gray center, with white specks | olivaceous black, then black with mummy brown edges |
| 15 | abundant, undulated surface; pale brown pigment excreted into medium | dawn gray center (later light mouse gray), changing into pale olive gray toward the edges | olivaceous black |
| 16 | abundant, smooth with some granules; good sporulation | light mouse gray; vegetative mycelium olive brown | olive brown center changing to blackish brown toward the edges, with cartridge buff edges |
| 17 | abundant, fairly smooth, wrinkled surface; good sporulation | mouse gray with white specks | olive black center turning black toward the edges; cartridge buff edges; later, uniformly black with hair brown edges |
| 18 | abundant, smooth or slightly coarse in places, with ruffled edges, raised; good sporulation | pale mouse gray with off-white spots | blackish brown center turning to black toward the edges |
| 19 | abundant, flat, elevated ridge near the edges; good sporulation | light mouse gray with few white specks | light grayish olive center, changing to chaetura drab toward the edges, and cartridge buff edges |
| 20 | abundant, smooth, raised, with cracking edges; brown pigment excreted into medium | pale olive gray at center changing to very pale olive gray near edges; vegatative mycelium chaetura drab to light drab | blackish brown at center, turning to avellaneous toward the edges (reverse of vegetative mycelium) |
| 21 | abundant, flat good sporulation | light mouse gray | mouse gray |
| 22 | good growth and sporulation | mouse gray with pale mouse gray spots | mouse gray |

In a selected group of carbon assimilation tests, this strain grew well on glucose and L-arabinose; growth on xylose was poor, and on fructose, raffinose and rhamnose it was doubtful. No growth was observed with sucrose, mannitol, myo-inositol and cellulose. The basal medium without any carbon source other than agar (Bacto, Difco) supported an appreciable degree of marginal growth.

Hydrolysis of gelatin was slightly positive after one day and frankly positive in four days. The reduction of nitrate was positive after 2 days incubation. The organism peptonizes the skim milk without formation of a curdle. Starch and casein are hydrolyzed; there is blackening of tyrosine, and decomposition of adenine, xanthine (slight) and hypoxanthine. No production of $H_2S$ has been detected on medium 22.

The species Streptomyces 372A described herein includes all strains of Streptomyces which form a compound of the Formula I and which cannot be definitely differentiated from the culture number 372A and its subcultures including mutants and variants. The compound of the Formula I is identified herein and after this identification is known, it is easy to differentiate the strains producing a compound of the Formula I from others.

Streptomyces sp. 372A, when grown under suitable conditions, produces a compound of the Formula I. A fermentation broth containing Streptomyces sp. 372A is prepared by inoculating spores or mycelia of the organism producing the compound of the Formula I into a suitable medium and then cultivating under aerobic conditions. For the production of a compound of the Formula I, cultivation on a solid medium is possible but for production in large quantities, cultivation in a liquid medium is preferable. The temperature of the cultivation may be varied over a wide range, 20°–35°C, within which the organism may grow but a temperature of 26°–30°C and a substantially neutral pH are preferred. In the submerged aerobic fermentation of the organism for the production of a compound of the Formula I, the medium may contain as the source for carbon, a commercially available glyceride oil or a carbohydrate such as glycerol, glucose, maltose, lactose, dextrin, starch, etc. in pure or crude states and as the source of nitrogen, an organic material such as soybean meal, distillers' solubles, peanut meal, cotton seed meal, meat extract, peptone, fish meal, yeast extract, corn steep liquor, etc. and when desired inorganic sources of nitrogen such as nitrates and ammonium salts and mineral salts such as ammonium sulfate, magnesium sulfate and the like. It also may contain sodium chloride, potassium chloride, potassium phosphate and the like and buffering agents such as sodium citrate, calcium carbonate or phosphates and trace amounts of heavy metal salts. In aerated submerged culturing procedures, an anti-foam agent such as liquid paraffin, fatty oils or silicone compounds is used. More than one kind of carbon source, nitrogen source or anti-foam source may be used for production of a compound of the Formula I.

The following Examples will serve to illustrate this invention without limiting it hereto.

EXAMPLE 1

Spores of Streptomyces sp. 372A were added to a 6-liter Erlenmeyer flask containing 2 liters of inoculum medium composed of (in g/liter): Bactopeptone (Difco), 6.0; N-Z Amine type A (Sheffield), 4.0; yeast autolyzate (Natural Yeast Products), 3.0; beef extract (Wilson), 1.5; and dextrose, 1.0. The flasks were incubated at 28°C for 96 hours on a rotary shaker 250 rpm with a 2 inch throw. Four liters of inoculum was then added to 230 liters of fermentation medium, containing (in g/liter): tomato paste (Contadina), 20; glycerol, 20; and calcium carbonate, 5. The pH was adjusted to 7 before sterilization. The culture was incubated in a 380-liter fermentor, aerated at 113 liters per minute and agitated at 280 rpm. Silicone antifoam (5% Dimethyl Siloxane) (Dow Corning AF) was added as needed to control frothing and the pH was maintained between 7.0 and 7.5 by addition of 5N sulfuric acid. After 72 hours the fermentation was filtered through infusorial earth by centrifugation. Two fermentations were run concurrently and the clarified broths were pooled prior to the isolation.

EXAMPLE 2

The filtered broths 460 liters, was applied to a column which contained 50 liters of Dowex 50WX4 resin (Styrene-Divinyl Benzene Sulfonic Acid Ion Exchange Resin), 50–100 mesh ($H^+$). The column was washed with 100 liters of distilled water and the activity was then eluted with 200 liters of 5% aqueous pyridine solution adjusted to pH 5.7 with 2.3 liters of glacial acetic acid. After evaporation under reduced pressure 73 g of solids, 0.3% pure, were obtained. This material was taken up in 350 ml of distilled water, adjusted to pH 3.2 and applied to a column, of Bio-Rad AG50W-X-4 resin, (Styrene-Divinyl Benzene Sulfonic Acid Ion Exchange Resin), 100–200 mesh ($Na^+$, 92 × 1000 mm). The column was eluted with 0.2M sodium citrate-phosphate buffer, pH 3.85. The activity appeared in a 5 liter fraction at an elution volume of 30 liters. The active fraction was desalted by readsorption onto 2 liters Bio-Rad AG50WX4 resin, 50–100 mesh ($H^+$) followed by elution with 10% aqueous pyridine solution. The eluate was evaporated under reduced pressure to 4.3 g solids, 5% pure. Material obtained from four 230 liter fermentations, purified as described above, was combined, taken up in 60 ml water, adjusted to pH 3.0, and applied to a column of Bio-Rad AG50WX4 200–400 mesh ($Na^+$, 41 × 1900 mm). The resin was eluted with 0.2M sodium citrate-phosphate buffer, pH 3.5. The activity appeared in a 4.3 liter fraction at an elution volume of 7.5 liters. This fraction was desalted as described above on a 1 liter column of AG50WX4 cation exchange resin, 50–100 mesh ($H^+$), and evaporated under reduced pressure to give 4.2 g of 19% pure material. This was taken up in 20 ml of n-butanol-acetic acid-water (12:3:5), and applied to a dry column, of Bio-Rad cellulose MX (Microcrystalline non-fibrous cellulose), (36 × 500 mm). The cellulose was eluted with the same solvent and the activity appeared in a 300 ml fraction at an elution volume of 240 ml. This was partially evaporated under reduced pressure, diluted with water to a homogeneous solution and applied to a 40 ml column of Bio-Rad AG50WX4, 50–100 mesh resin ($H^+$). The activity was eluted with 15% aqueous pyridine solution, the eluate concentrated under reduced pressure, and (I) was crystallized in two crops from aqueous methanol to give 434 mg single spot material. The mother liquors from the original crystallization were rechromatographed on another cellulose column, (18 × 800 mm). After repetition of the above described treatment an additional 82 mg (I) crystallized.

This was combined with the previously obtained material and recrystallized to give final product. (I); Anal. calcd for $C_{10}H_{16}ClN_3O_5$; C 40.89, H 5.49, N 14.31. Found: C 41.07, H 5.57, N 14.11, mp 220°–225° (dec with release of NH₄Cl); overall purification, 3200 fold; overall recovery, 44%; ir 1745 (lactam) 1710, 1680 (amide), 1635 cm⁻¹ (carboxylate); nmr (D₂O, DCl, 15 mg, ext TMS), 5.33 (dd, 1, J = 6.5 and 8 Hz, Cl—CH—CH₂), 4.90 (dd, 1, J = 6.5 and 9 Hz, CH₂—CH—C), 4.78 (q, 1, J = 7Hz, CH—CH₃), 4.09 (d, 1, J gem = 13.5 Hz, C—CH₂—N), 3.87 (d, 1, J gem = 13.5 Hz, C—CH₂—N), 2.92 (m, 2, CH—CH₂—CH), 2.13 (d, 3, J = 7 Hz, CH—CH₃).

EXAMPLE 3

As indicated above, the compound of the Formula I is active against gram-positive bacteria and can be employed in the treatment in control of diseases caused by these organisms. Listed in mm. Table I which follows are the inhibition zone diameters, in an agar-diffusion test procedure employing paper discs on minimal agar medium. Listed in Table 2 are zone diameters of inhibition observed in agar-cup diffusion assay employing stainless steel cylinders and complex nitrogenous agar medium. As is apparent from the foregoing properties, the antibiotic of the Formula I is useful for suppressing the growth of gram-negative and gram-positive organisms in a defined medium and gram-positive in complex medium.

The compound of the Formula I also evidenced antimetabolite activity. This activity was determined by counter diffusion methods which have been described in the literature in Journal of Antibiotics Volume 27 pp. 229–233, 1974 against all microorganism in Table I. The activity of the compound of the Formula I was reversed by the addition of L-Glutamine to the medium. Other common amino acids, nucleosides and water soluble vitamins did not reverse the activity of a compound of the Formula I.

Table i

| Artimicrobial Spectrum Microorganism | Inhibition zone diameter* (mm) |
|---|---|
| Bacillus cereus ATCC-6464 | 66 |
| Bacillus subtilis NRRL-558 | 22 |
| Bacillus sp. ATCC-27860 | 17 |
| Streptomyces cellulosae ATCC-3313 | 40 |
| Escherichia coli B | 60 |
| Klebsiella pneumoniae ATCC-27858 | 44 |
| Serratia sp. | 37 |

*Paper discs (12.7 mm dia) containing approximately 12 μg of (I) were placed on agar surfaces previously seeded with the test organism.

Table 2

| Test Microorganism | Concentration (Mcg/ml) | Inhibition zone diameter (mm) |
|---|---|---|
| Bacillus megaterium | 10 | 15 |
| ATCC 8011 | 100 | 30 |
| Sarcina lutea ATCC 9341 | 10 | 14 |
| | 100 | 30 |
| Staphylococcus aureus | 10 | 0 |
| ATCC 6538P | 100 | 12 |

As is indicated above, the compound is prepared under submerged aerobic conditions. Preferably submerged fermentation in tanks is used for production of substantial quantities of the 372A antibiotic in accordance with conventional procedures. Small quantities of antibiotic are obtained by shake-flask culture. As is customary in aerobic submerged culture processes, sterile air is blown through the culture medium. For efficient growth of the organism and production of the antibiotic of the Formula I, the volume of air employed in the production is above 0.1 volume of air per minute per volume of culture medium. Optimum growth occurs when the volume of air employed is between 0.5 and one volume of air per minute per volume of culture production medium. The production of antibiotic can be followed during the fermentation by testing samples of the broth for antibiotic activity against organisms known to be sensitive to the antibiotic. The bioassay is conveniently effected by paper disc assay on agar plates.

As is the custom, maximum antibiotic production occurs within 2–6 days in either large tank or shake-flask fermentation. Commonly maximum production of antibiotic activity is realized within 3–4 days.

Following its production under submerged aerobic conditions the compound of the Formula I can be recovered from the fermentation broth by methods commonly employed in the fermentation art. The antibiotic activity produced during fermentation of a compound of the Formula I—producing organism occurs in the antibiotic broth. Accordingly, isolation techniques employed in the production of such antibiotics are designed to permit maximum recovery of the antibiotic from the broth. Thus, for example, mycelia and undissolved solids are removed from the fermentation broth by conventional means such as filtration and the antibiotic of the Formula I is recovered from the filtered broth by techniques such as Ion exchange or adsorption.

The compound of the Formula I having the basic amino group can form salts with acids. The compound of the formula I can form salts with acid substances and such substances can be prepared by conventional techniques with such pharmaceutically acceptable acids as hydrochloric acid, hydrobromic acid, sulfuric acid and the like. All that is required of the salt is that it provide a pharmaceutically acceptable salt of a compound of the Formula I.

As is indicated above, compounds of the Formula I and its salts which has the property of adversely affecting the growth of certain gram-positive bacteria. It is useful in wash solutions for sanitary purposes as in the washing of hands and the cleaning of equipment, floors or furnishings of contaminated rooms or laboratories; It is useful also for suppressing the growth of sensitive organisms in plate assays and other microbiological media.

We claim:

1. A process for the production of an antibiotic substance of the formula:

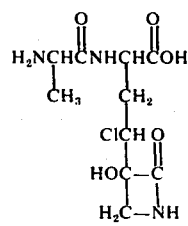

wherein all of the optically active sites are in the S configuration, which comprises cultivating a strain of Streptomyces Sp. 372A, NRRL 8045 in an aqueous carbohydrate solution containing a nitrogenous nutrient under submerged aerobic conditions until activity versus gram-positive and gram-negative bacteria is imparted to said solution and then recovering said antibiotic of the Formula I from said solution.

* * * * *